United States Patent [19]

Ackerman

[11] 4,218,541

[45] Aug. 19, 1980

[54] CONVERTING UREA WITH BACTERIA

[76] Inventor: Roy A. Ackerman, P.O. Box 5072, Charlottesville, Va. 22903

[21] Appl. No.: 891,976

[22] Filed: Mar. 30, 1978

[51] Int. Cl.$^2$ ................................................ C12B 1/00
[52] U.S. Cl. .................................... 435/262; 435/268; 435/822; 435/832; 435/874; 435/885; 210/22 A
[58] Field of Search ..................... 195/2; 435/262, 268

[56] References Cited
PUBLICATIONS

Stanier et al., The Microbial World, 1970 pp. 56-59.

*Primary Examiner*—Lionel M. Shapiro
*Attorney, Agent, or Firm*—Pollock, Vande Sande & Priddy

[57] ABSTRACT

Urea such as that present in dialysates is converted to inocuous products by employing a culture having the identification ATCC 31381 or one of its primary cultures or mixtures thereof.

8 Claims, 5 Drawing Figures

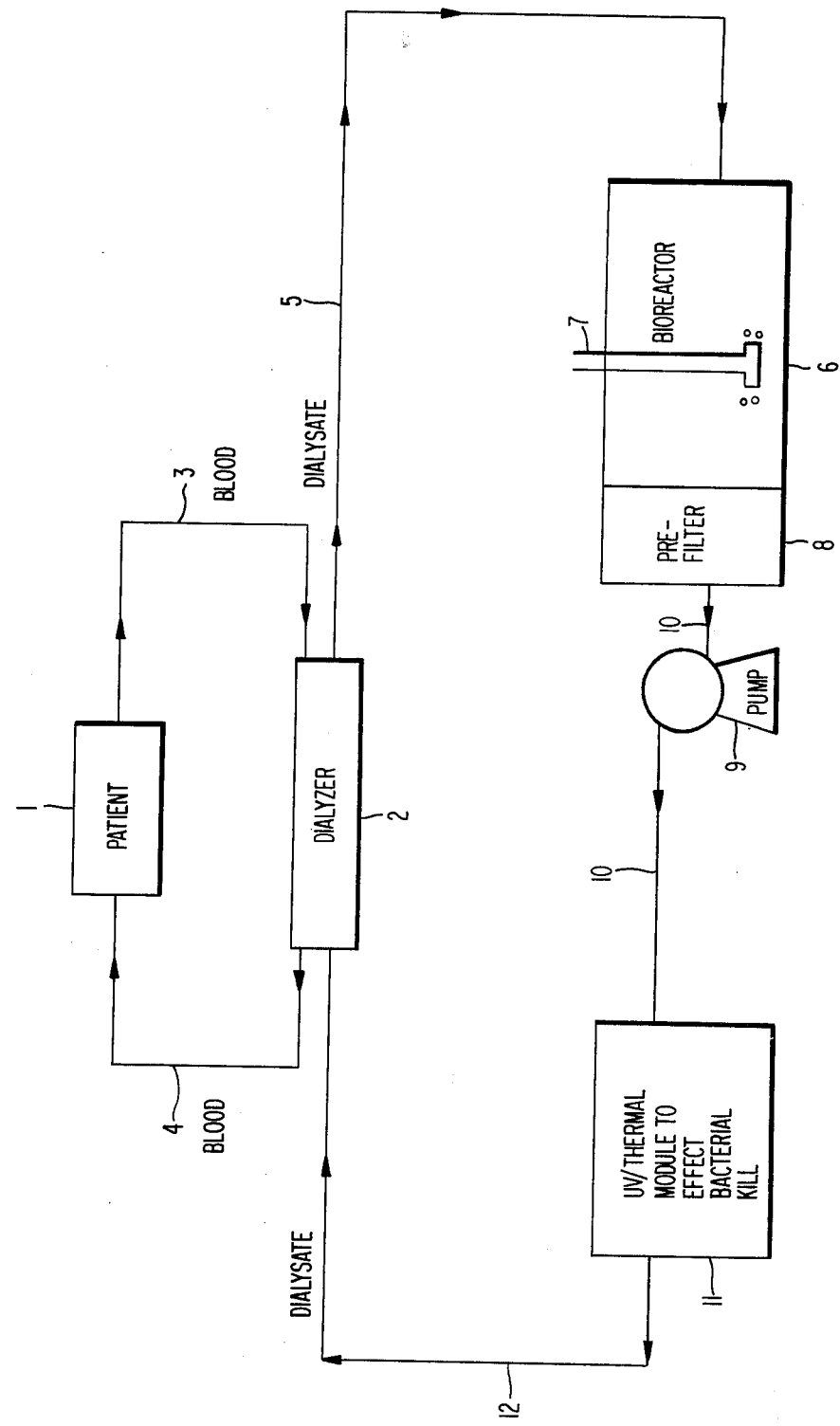

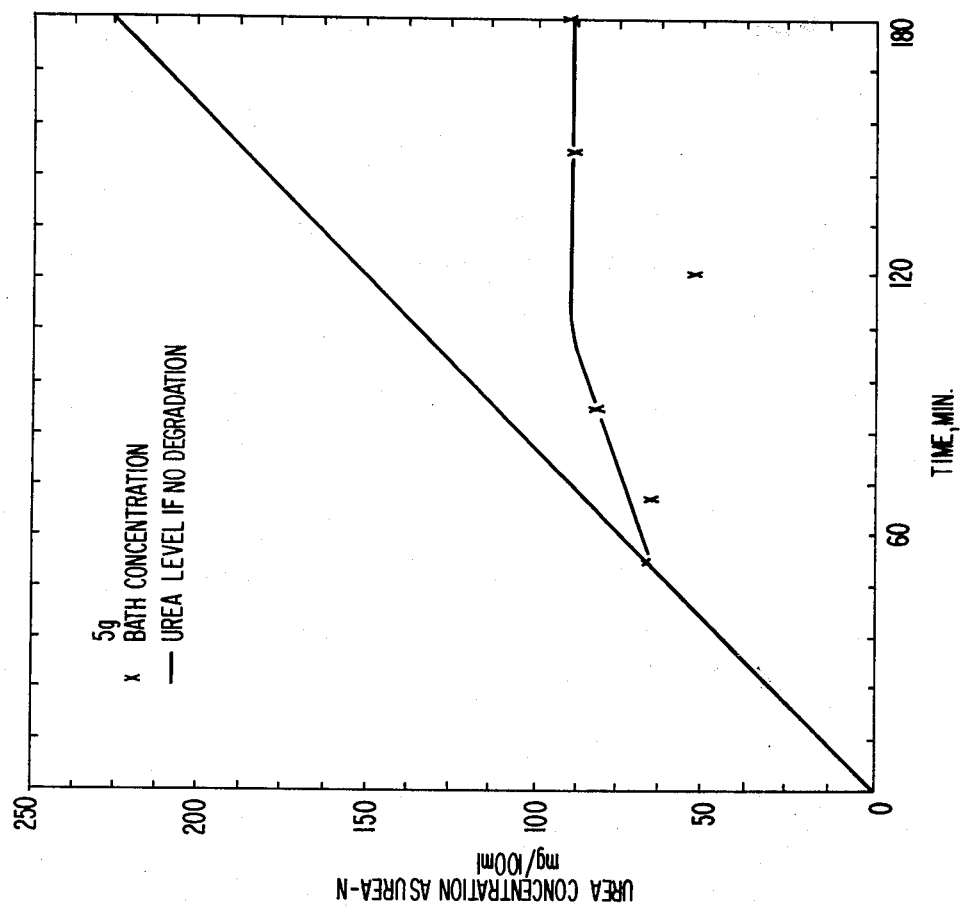
FIG 3 CONTINUOUSLY INFUSED UREA
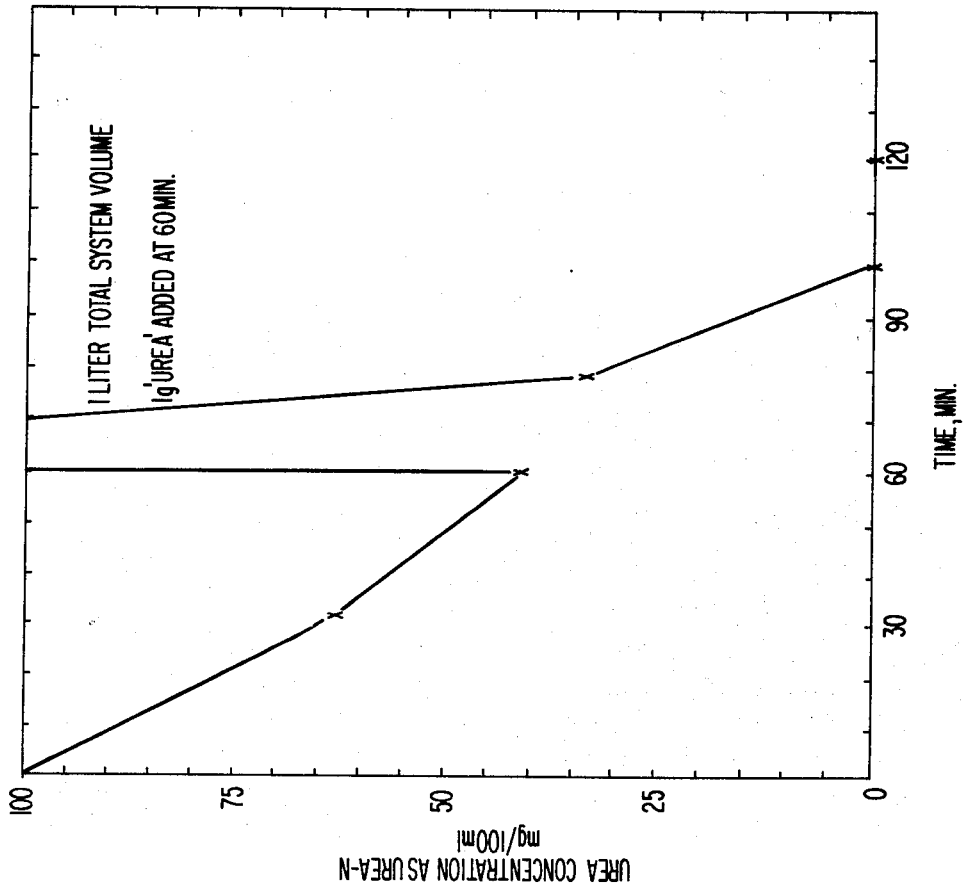
FIG 2 DEGRADATION OF BATCH-FED UREA

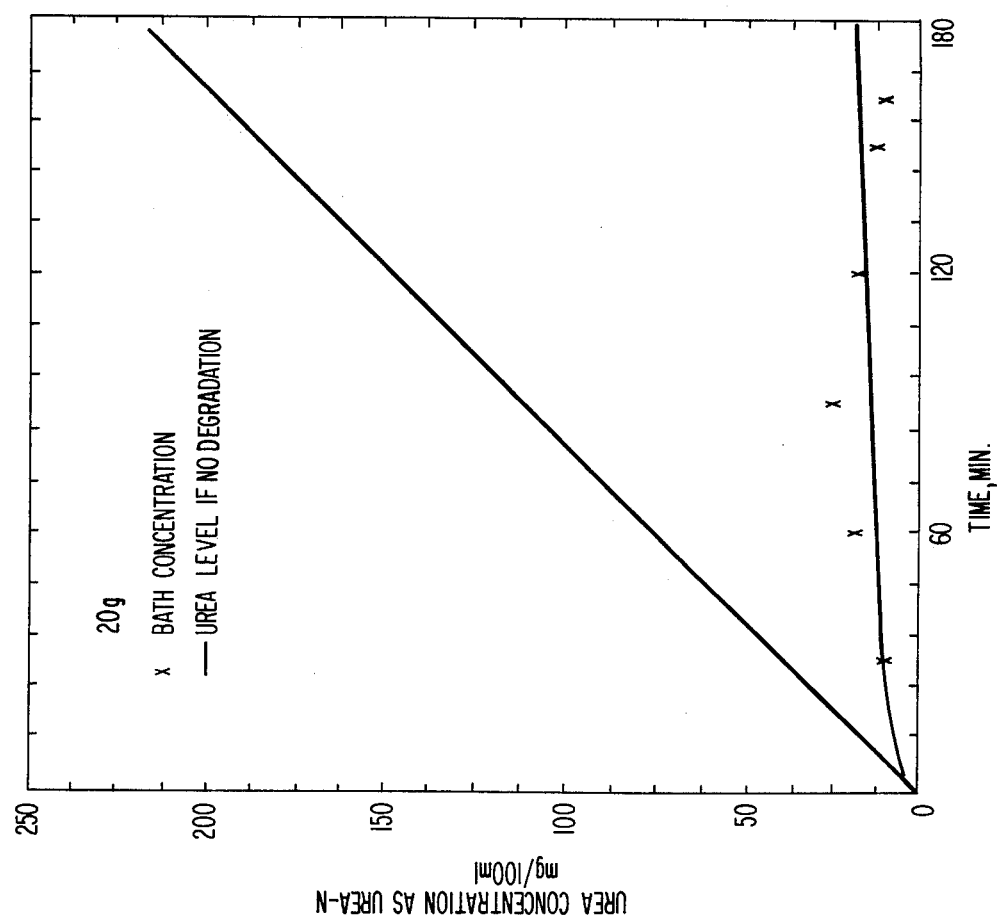
FIG 5  CONTINUOUSLY INFUSED UREA
20g
× BATH CONCENTRATION
— UREA LEVEL IF NO DEGRADATION
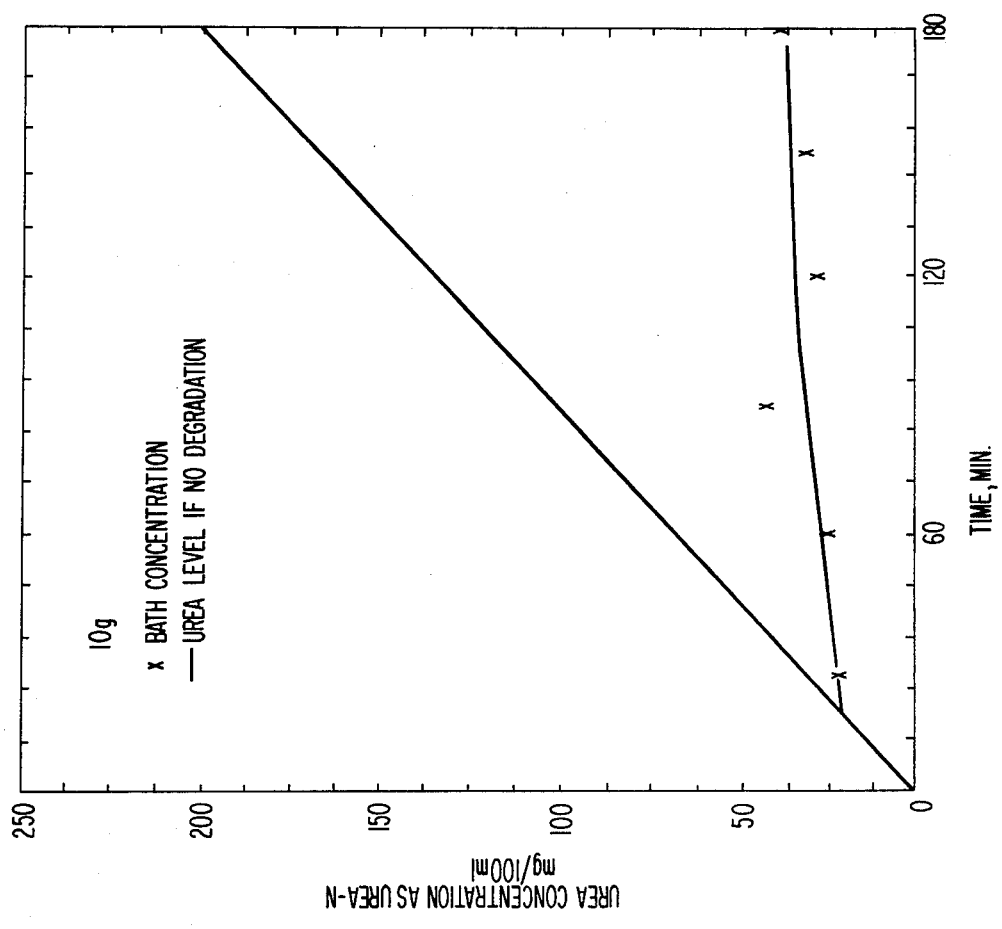
FIG 4  CONTINUOUSLY INFUSED UREA
10g
× BATH CONCENTRATION
— UREA LEVEL IF NO DEGRADATION

CONVERTING UREA WITH BACTERIA

CROSS-REFERENCE TO RELATED APPLICATIONS

The present application is related to my copending application Ser. No. 891,975 filed Mar. 30, 1978 entitled "Method of Growing A Deammonifying Culture and Use Thereof in Wastewater Treatment", and embodies the invention disclosed in Invention Disclosure Document 056382 filed Dec. 27, 1976, disclosure of which is incorporated herein by reference.

FIELD OF INVENTION

The present invention is concerned with oxidizing or converting urea and particularly urea present in dialysates. In particular, the present invention is concerned with the use of certain nitrogen-metabolizing bacteria. For convenience, the present invention will be described with particular emphasis on treating dialysates. However, it is understood that the present invention is applicable to converting urea in general to products inocuous to humans.

BACKGROUND OF INVENTION

Enzymatic reactors are finding employ in leukemia therapy, dialysis, and hepatic support. In addition, whole microbial cells are being tested and systems developed for their suitability as artificial organs.

An artificial organ is a device that will hopefully replace or augment the diseased, damaged, or malfunctioning one. By and large, these devices are only able to perform one or two of the vital functions of the replaced or assisted human organ. One of the most studied artificial organs—as well as the most widely used—is the artificial kidney (or dialyzer). In this country alone, about 60,000 people die annually of renal failure. The only effective means of treating kidney ailments today is through the use of dialysis. Unfortunately, artificial kidneys are not as efficient nor as convenient as they should be.

To maintain the consistency of the human internal environment, the actual kidney performs several functions: It detoxifies certain organic compounds; it synthesizes both hormones and enzymes; it excretes waste; and it also maintains the balances for water, electrolytes, and acids and bases. In performing these body functions, the kidney regulates the concentration of most of the plasma constituents; these include urea, uric acid, creatinine, phenols, water, and the ions of sodium, potassium, calcium, magnesium, bicarbonate, chloride, phosphate, and sulphate.

Some 32,000 patients are treated by dialysis in the U.S. The artificial kidney supplements and in most cases performs extensively, one of the major body functions—the removal of certain potentially toxic substances all of which are soluble in water, from the body. At times, the dialyzer is also called upon to remove excess body water; this is typically removed by ultrafiltration techniques (the imposition of negative pressure on the blood within the dialyzer). However, since we do not know what the exact toxic substances are, we cannot determine if they are adequately removed. (Three of the currently accepted uremic toxin markers are urea, creatinine, and uric acid). Moreover, these artificial kidneys are non-physiologic and use passive mass transfer, instead of the complex, nephronic processes. This limits the efficiency of the therapy, so the search for more physiologic and efficient processes is still ongoing.

The supply system for the dialyzer typically is a one-pass type. A saline concentrate is mixed with deionized water to produce a set flowrate of influent dialysate. The supply is preheated to 37°–39° C. to maintain the blood temperature in the extracorporeal circuit. The produced dialysate is continuously monitored to insure that it is at the correct concentration. A batch system (which requires a large tank of premixed solution), on the otherhand, requires an initial supply of 120–400 liters of deionized water. Such a large supply volume might be an inconvenience for the hospital to provide, but it is virtually impossible for the home dialysis patient to maintain.

For several years now, adsorption devices have been available to provide a dialysate supply system that utilizes a rather small volume (5–30 liters) of water, compared to 120–400 l volumes required for the standard dialysis procedure. The sorbents employed include activated carbon, zirconium phosphate, zirconium oxide, alumina, along with urease. By and large, these systems are limited in their ability to remove urea from the dialysate solution, even with the urease enzymes present. The increased urea concentration therefore reduces the driving force available to effect mass transfer from the blood. Examples of such systems are suggested by Gordon, Bergstrom, Rosenfeld & Maxwell in *Adsorption of Uremic Toxins*. VI International Congress of Nephrology; Florence, Italy, June, 1975, and Maeda, Ohta, Manji, Saito, Kawaguchi, Amano, Shibata, & Kobayashi. Dialysate regeneration: 30 liter dialysate supply system with sorbents. *Kidney International.* 10, S 289-S 295 (1976).

Around 1966, CCI Life Systems, Inc. employed a system which uses about 5.5 liters of dialysate. It is a self-contained unit (once the initial water is supplied) that maintains the dialysate concentration within normal limits. The metabolic wastes products contained by the returned dialysate are absorbed by the cartridge so that no build-up of uremic toxins occurs. The regeneration system is comprised of activated carbon, zirconium phosphate, zirconium oxide, and urease. The urease converts urea to ammonia, which together with calcium and magnesium ions, is exchanged for sodium and hydrogen ions on the zirconium phosphate. Phosphate is removed via the zirconium oxide, and the activated charcoal removes other organic metabolites.

There are some major problems with this system. First of all, the dialysate flow cannot exceed approximately 250 ml/min due to the excessive pressure drop through the cartridge. This requires a lengthened dialysis treatment; an increase in time the patient must be connected to the dialyzer. In addition to this problem, the removal of metabolic waste products from the dialysate are not complete, and ammonia builds up, further decreasing the rate of dialysis.

Paul Malchesky and Yokihiko Nose of the Cleveland Clinic Foundation have been examining the use of microbial reactors as artificial kidneys. Malchesky and Nose hope to culture a bacterial population that can remove and possibly recycle urinary waste products. Since the solute removal is a function of the medium composition, the removal rates could be adapted to the patient's requirements.

Some literature concerning this development by Malchesky and Nose includes Malchesky PS & Nose Y. 1977. Biological Reactors for Renal Support. Presented at the 23rd Annual Meeting of the Amer. Soc. Art. Inter. Organs. Montreal, Canada. 22 April; Malchesky PS and Nose Y. 1975. Biological Reactors as Artificial Organs. *Cleveland Clinic Quarterly.* 42,3:267-271; Malchesky PS and Nose Y. 1974. The Use of Biological Reactors as Artificial Organs. Presented at the 27th Ann. Conf. Eng. Med. Bio. Philadelphia, Pa. October 6-10; and Malchesky PS, Fingerhood B., Nose Y., Gavan T., & Willis C. 1976. The Use of Microorganisms for Renal Support. Presented at the 29th Ann. Conf. Eng. Med. Bio. Boston, Mass. November 6-10.

Their method involved the culturing of activated sludge bacteria and some supplementary species (i.e. Rhizobium) with normal urine. While the ideal support system might be subjected to different quantities of metabolic by-products (since normal, as opposed to uremic urine is used), the actual requirements should be identical.

The basic system uses a stirred aerobic vessel containing 900 ml of urine and an inoculum of $5 \times 10^5$ bacteria. Temperatures ranged from 20°-37 ° C. Each batch culture was maintained for 3-4 daily pH adjustments. This culture then served as the inoculum for the subsequent reactor.

To date, some 110 systems have been studied. They found that urea and uric removals were substantial (74 and 64%, respectively) and the creatinine reduction was 25%. Almost half the time, the urea was completely removed from the culture. Malchesky and Nose attribute the failure to consistently remove urea completely to contamination or a build-up of ammonia between pH adjustments. (For those times that urea was completely removed, higher uric acid and creatinine removals were obtained).

Overall then, Malchesky and Nose found that their cultures removed 6.6 g/d of urea, 163.5 mg/d of creatinine, and 145.5 mg/d of uric acid. Excess calcium, phosphate, and potassium were also removed, but to a smaller degree. In addition, they found that there were adptation periods required before the bacterial density increased. These studies were designed to verify culture selection and not the final consumption rates. Now that they have adequate bacterial stock cultures, they will begin continuous culture studies to determine the system feasibility.

While the utilization of one biological system (bacteria) that requires the waste products of another living thing (human being) is a symbiotic, physiologic relationship, the potential problems with such a system are numerous. The most important of these are the possible infections that could result from the utilized bacterial system which can come into contact with the patients blood supply or from possible pyrogenic reactions within the patient.

Asher and his co-workers at Exxon have been developing an adsorbent system to remove toxins from the gastro-intestinal tract. For instance, see Asher W. J., Vogler T. C., Bovee K. C., Holtzapple P. G., & Hamilton R. W. 1976. Projections and measurements of in vivo performance of liquid membrane capsules. *Kidney International.* 10:S2540258; Asher W. J., Vogler T. C., Bovee K. C., Holtzapple P. G. & Hamilton R. W. 1976. In vivo performance of liquid membrane capsules. *Trans. Amer. Soc. Artif. Intern. Organs.* XXII; and Asher W. J., Vogler T. C., Bovee K. C., Holtzapple P. G., & Hamilton R. W. 1977. *J. Dial.* 1, 3:261-284.

They have been working with liquid membrane capsules (LMC). These LMC contain stabilized drops of emulsion suspended in a continuous phase. The capsule diameter ranges about 375 microns, with microdroplets of 1 to 5 micron diameter in their interior.

Urea diffuses from the blood into the intestine. The urease enzyme in the capsule converts the transported urea to carbon dioxide and ammonia. The ammonia is trapped within the LMC and excreted, while the carbon dioxide is eliminated by the lungs.

To obtain effective trapping of the uremic "toxin", the following criteria must be met:
1. Mucosal membrane transport must be sufficient.
2. The LMC should not greatly affect the mucosal membrane transport.
3. The LMC must remove the toxin under the conditions present within the intestinal lumen.
4. The LMC should not damage the intestinal mucosa.
5. The urease enzyme must be protected from the acidic stomach environment.
6. The LMC should be stable to bile concentrations.
7. Pancreatic secretions, due to their proteolytic activity, should not reduce the urease activity below the level required.

The first four requirements have been met by the general nature of the LMC. To prevent any damage to the urease in the stomach and to maintain the LMC effectiveness in the intestine, the oil phase contains monoolein and two different types of LMC are used. One LMC encapsulates urea and the other encapsulates the citric acid, which is the ammonia trapping agent.

The pancreatic secretion releases the urease enzyme from the LMC, where it is exposed to the secretion's proteolytic activity. These effects seem to be counter—balanced so far—a higher concentration of pancreatic secretion releases more urease, which is then exposed to a higher proteolytic activity. Therefore, a constant urease concentration is available for urea converstion.

The expected urea removal is on the order of 24 g/d for humans. (To date, the LMC formulations have only been tested on dogs). Thus, a milk shake comprised of these LMC might prove to be another valuable adjunct to dialysis. Additional LMC might be developed to handle other uremic toxins.

TMC Chang at McGill has been studying "artificial cells" for well over 2 decades. The cells are in the form of micro encapsulated enzymes, cells, cell extracts, adsorbents or other biologically active materials. The encapsulating membranes have a molecular weight cutoff of about 5000, a thickness of 200 A, and a large surface area to volume ratio.

Chang has used these cells to remove urea from the body (microencapsulated urease); treat mice with acatalasemia, a congenital enzyme deficiency (microencapsulated catalase); treat lymphosarcoma (microencapsulated asparaginase); and remove toxins and waste products (microencapsulated absorbents).

For instance, see Chang TMS. 1974. A Comparison of Semipermable Microcapsules and Standard Dialyzers for Use in Separation. *Sep. Purif. Meth.* 3, 2: 245-262; Chang TMS. 1975. Microencapsulated adsorbent hemoperfusion for uremia, intoxication, and hepatic failure. *Kidney International.* 7; S387-S392; Chang TMS. 1976. Microcapsule artificial kidney. Including updated preparative procedures and properties. *Kidney International.* 10:S218-S224; and Chang TMS. 1976. Hemoperfusion alone and in series with ultrafiltration or dialysis for uremia, poisoning, and liver failure. *Kidney International.* 10:S305-S311.

Chang has recently combined the first and last techniques to improve on the dialysis procedure.

Chang has found that the clearances for a renal support device are 230 ml/min for creatinine, 100 ml/min for middle molecules, and greater than 200 ml/min for toxic drugs. These values are from two to ten times greater than the rates achieved with conventional treatment. The microencapsulated urease is capable of reducing the blood urea concentration by 50% within 90 minutes. The urea is converted to ammonia with the microencapsule, so an ammonia trapping agent is required, as Asher's method does.

Because the ammonia trapping agent was a fairly new development, Chang has only reported clinical data for the use of the microencapsulated absorbent (activated charcoal system) in conjunction with a 0.2 $m^2$ (membrane area) ultrafilter. He found that 2 hours of hemoperfusion with this system was as effective as 6 to 8 hours of treatment with a standard (1–2 $m^2$) dialyzer.

The system suggested by Chang is somewhat similar to the system by CCI Life Systems referrd to hereinabove. There are many other experimental programs using enzymes and bacteria in dialysis. For example, Ioakim and Rosen at the University of London are working on a urease—ion exchange—carbon system.

For a discussion of the use of enzymes, see the article by applicant entitled Microbial and Enzymatic Systems Serve as Artificial Organs, Ackerman, R.A. SIM News, Sept., 1977, p. 4 ff.

An object of the present invention is to provide a microbial system for converting urea and especially a microbial system as a dialysate regenerator, which system is capable of digesting the waste products of the patient. A further object of the present invention is to provide a dialysate supply system capable of providing a sterile dialysate at normal flow rates (e.g., about 500 ml/min) to any currently available dialyzer.

The present invention makes it possible to employ a low-volume dialsate supply device (e.g., about 10 leters of water or less) while providing for relatively high dialysate flow rates (250—1000 ml/min) as compared to currently available low-volume dialysate supply devices.

By employing the present invention, a sterile dialysate is dispensed. According to the present invention, certain nitrogen-metabolizing strains of bacteria are employed which degrade the chemicals in the dialysate that were removed from the blood. The bacteria employed is capable of degrading nitrogenous compounds to gaseous products, leaving no residue within the culture.

SUMMARY OF INVENTION

The present invention is concerned with the use of a culture identified as ATCC 31381 or one or more of the primary cultures thereof to convert the urea therein to an inocuous product and especially to treat a dialysate used in hemodialysis.

BRIEF DESCRIPTION OF THE DRAWINGS

FIG. 1 is a schematic diagram of a dialysate regenerator employing the present invention.

FIG. 2 is a graph showing degradation of batch-fed urea.

FIGS. 3, 4, and 5 are graphs showing urea degradation at 5 grams, 10 grams, and 20 grams, respectively, of ATCC 31381.

DESCRIPTION OF PREFERRED EMBODIMENTS

The microorganisms employed in the present invention are those identified as ATCC 31381 or one or more of its primary cultures, or mixtures thereof. The cultures are preferably added on a semisolid substrate of peanut hulls containing up to 12% by weight based on the peanut hulls of a cereal grain as used for growing the cultures. However, if desired, the culture can be added per se and not on a substrate.

The details of a method for growing the cultures are disclosed in my copending U.S. Patent application, filed concurrently herewith and entitled "Method for Growing a Deammonifying Culture and Use Thereof in Wastewater Treatment", disclosure of which is incorporated herein by reference. Also, see Ackerman et al, "Development in Industrial Microbiology", Vol. 18, Chapter 36, The Commercial Preparation of Nitrifying Cultures on Semi-Solid Substrate, 1977, pages 457–462.

In particular, the medium suitable for growing the microorganisms is a semisolid medium containing peanut hulls, water, a carbonate source, an ammonia source, and a phosphate source. The carbonate source is employed in amounts sufficient to provide the medium with a pH in the range from about 5 to 9. The ammonia source is present in amounts sufficient to assure that the ammonia is not depleted during the process. The peanut hulls are present in amounts sufficient to provide adequate sites for growth of the microorganism. The water is added to a semisolid medium to facilitate mixing and contact of the culture and nutrients with the peanut hulls. The amount of water is usually present in an amount to provide a water-substrate ratio within the range of about 1.3:1 to about 0.7:1.

In addition, if desired, the medium can optionally contain a magnesium source, a chloride source and trace amounts of such metals as iron, zinc, copper, molybdenum, cobalt, and manganese. It is recognized that these additional materials are not always (or may not be) necessary. The medium can also contain about 12% by weight based upon the weight of the peanut hulls of a cereal grain such as wheat bran, rice bran, oat hulls, soybean hulls and the like. For a discussion of nutrients, attention is directed to MS. Finstein et al, [*Water Research*, 6; pp. 31–40 (1972)].

Also, it is preferred that growth of the culture be initially conducted in a solution of the desired nutrients to develop a suitable mass of microorganism to be added to the peanut hull substrate. By using this two-stage preparation, mixing the various components is easier since the nutrients and culture are in a liquid. Also, this procedure helps assure adequate contact of the culture with the substrate. The use of two steps also makes it possible to reduce the time used to grow the microorganism. Growth in the liquid medium is generally carried out for about 1 to 5 days until a satisfactory biomass is obtained, which can be observed by the formation of small brown pin-like flocs.

The microorganisms employed can be that identified as ATCC 31381 and/or one or more of the primary cultures thereof. The primary cultures can be obtained from the microorganisms identified as ATCC 31381 by standard separatory procedures for bacterial isolation. For instance, see Isolation of Pure Cultures by Plating Methods (*The Microbial World*—R. Y. Stanier et al, Prentice Hall, New Jersey, 1970). It is believed that the primary cultures include Enterobacter agglomerans, a Group D Streptococcus, at least one and possibly two Bacilli, and at least one and possibly two Pseudomonads. The primary cultures have been isolated with Hektoen's agar plates and with Finstein's media.

The microorganisms are grown under aerobic conditions. The microorganisms identified as ATCC 31381 are on deposit at The American Type Culture Collection, 12301 Parklawn Drive, Rockville, Maryland. Access to the culture will be available during pendency of this patent application to anyone determined by the Commissioner of Patents to be entitled thereto under 37 CFR 1.14 and 35 USC 122. All restrictions by applicant on the availability to the public of the culture so deposited will be irrevocably removed upon the granting of the patent. The culture is now available to the public and the culture will be permanently available to the public through a depository affording permanence of the deposit and ready accessibility thereto by the public if the patent is granted.

The following method is presented to further illustrate the growth of the microorganisms.

About 1 gram of microorganism identified as ATCC 31381 is added to the medium described hereinbelow in Table 1. Aeration (either mechanical aeration or shaker culture) is then supplied for one (1) to five (5) days, until a satisfactory biomass is developed (light brown pin-like flocks are usually observed).

The semisolid culture medium described hereinbelow in Table 2 is then inoculated with the inoculum culture produced above. Generally about 1 to 30 liters of the inoculum are used. It is understood that microorganisms of the type ATCC 31381 need not be added initially to the medium described in Table 1 but can be added directly to the semisolid culture medium.

Table 1

| Culture medium employed for shake-flask test | |
|---|---|
| $CaCO_3$ | 10.0 g |
| $(NH_4)_2SO_4$ | 1.5 g |
| $K_2HPO_4$ | 0.5 g |
| $MgSO_4$ | 50 mg |
| $CaCl_2 . 2H_2O$ | 20 mg |
| $KHCO_3$ | 30 mg |
| tmm[a] | 1 ml |
| tap water | 1 liter |

[a]The trace metal mixture was of the following composition (g/liter): $FeSO_4.7H_2O$, 0.028; $ZnSO_4 . 7H_2O$, 0.140; $CuSO_4 . 5H_2O$, 0.025; $NaMoO_4 . 2H_2O$, 0.024; $CoCl_2 . 6H_2O$, 0.024; $MnSO_4 . H_2$, 0.084.

Table 2

| Semisolid medium composition used to produce final product culture | |
|---|---|
| Ground peanut hulls | 15.0 kg |
| $CaCO_3$ | 454 g |
| $(NH_4)_2SO_4$ | 100 g |
| $K_2HPO_4$ | 10 g |
| $MgSO_4$ | 1.0 g |
| $CaCl_2 . 2H_2O$ | 0.5 g |
| $KHCO_3$ | 0.75 g |
| Tap water | 7 liters |
| tmm[a] | 25 ml |

[a]The trace metal mixture was of the following composition (g/liter): $FeSO_4 . 7H_2O$, 0.028; $ZnSO_4 . 7H_2O$, 0.140; $CuSO_4 . 5H_2O$, 0.025; $NaMoO_4 . 2H_2O$, 0.024; $CoCl_2 . 6H_2O$, 0.024; $MnSO_4 . H_2O$, 0.084.

The medium was prepared by thoroughly mixing the water and the ground peanut hulls in a Hobart mixer, and then it was autoclaved. The substrate was cooled to about 25° C. after which it was inoculated with about 1.5 liters of the nitrifying inoculum produced above. This substrate with about 55–60 wt% moisture was placed in layers 2.5 cm thick on sterilized, perforated, stainless-steel trays. After a five-day incubation period at 24° C. and a minimum of 90% humidity, the incubator was reduced to 20% humidity. The material was then allowed to dry for 2 days to approximately 10% moisture to provide the desired product.

As discussed hereinabove, the primary cultures have been isolated on Hektoen's Agar Plates and on Finstein's media. If desired, these cultures can be used as inoculum sources. One loop of each culture is transferred to a vessel containing a small portion of sterile medium identified in Table 1. Aeration is then effected. Each day additional sterile medium is added until the desired volume has been added. The culture is then allowed to develop for an additional one (1) or two (2) days. This then serves as the nitrogen metabolizing inoculum to the semisolid system described above.

Moreover, if desired, any number of the primary cultures can be mixed with each other and/or with the culture identified as to provide desired relative amounts of any number of these primary cultures. This makes it possible to tailor-make a microbial product for a specific purpose or problem.

The original material from which the microorganisms ATCC 31381 was produced involved removing 100 ml of fluid from the aerobic chamber from two of applicant's waste treatment test units. These samples were mixed together and grown using the medium described in Table 1. Five milliliters of the fluid mixture from the unit served as the inoculum for each of 121-liter flasks which contained 250 ml of sterile medium. The temperature was maintained at 28±1C. After 1 wk., the ammonia levels in the flasks were determined. Of these flasks, eight had converted >50% of the initial ammonia to nitrate. These eight flasks then served as inoculum for the second selection phase in the medium described in Table 1. This time all 12 flasks provided >80% ammonia converstion.

These cultures were then grown on the semisolid substrate identified in Table 2.

Reference to FIG. 1 illustrates one system which can be used employing the process of the present invention wherein a patient is treated with a dialysate for conveying blood from the patient via tube 3 to dialyzer 2 and then returning the treated blood to the patient via tube 4. Contaminated dialysate is removed from dialyzer 2 via conduit 5 and conveyed to bioreactor which contains a culture identified as ATCC 31381 and/or one or more of its primary cultures.

The dialysate is aerated by injecting air, pure oxygen or other oxygen-containing gas via 7. The flow rate of the gas is such as to provide a dissolved oxygen content of at about 1 milligram/liter of dialysate. For a dialysate flow rate of 500 ml/min, about 0500–600 ml/min of oxygen were employed. Typical flow rates of dialysate treated range from 250–1000 ml/min. The temperature of the treatment with the culture can range from about 0 ° to about 40° C. and in this embodiment is preferably at normal body temperatures.

The treated dialysate can then be passed through a filter 8 to filter out large sized molecules. If desired, the filter can be placed before the bioreactor 6. Some suitable commercially available filters include AMP-Cuno Zeta plus and Millipore filters.

The dialysate is then conveyed by means of pump 9 and conduit 10 to a thermal or ultraviolet light treating unit 11 to kill the added culture and any other bacteria which might be in the dialysate. A typical ultraviolet light treatment is a dosage of about 100,000 microwatts-sec/cm². A typical thermal treatment is a temperature of about 160° F. for about 10 minutes. When a thermal treatment is employed, the temperature of the dialysate can be readjusted by a subsequent heat exchanger (not shown).

The dialysate is then returned to dialyzer 2 via conduit 12 for reuse. The dialyzer can be employed with any suitable saline type aqueous dialysate. The selection of a dialyzer to be used can be readily determined by persons skilled in the art. One suitable type of dialyzer is disclosed in U.S. Pat. No. 3,962,075 to Fialkoff et al. Also, if desired, the dialysate can be replenished with any ions if required prior to reentry into the dialyzer. Such ions can conveniently be added after pump 9 and prior to treatment vessel 11.

Moreover, it might be desirable to also employ an adsorbent in the system such as activated carbon to remove higher molecular weight uremic toxins such as creatinine. The activated carbon could be employed before, after, or at the same time as the culture is used. In fact, the bacteria per se and/or in combination with the substrate can be immobilized on the activated carbon and employed in such manner.

The amount of culture employed is primarily dependent upon the amount of urea in the material being treated, and can vary over a wide range. Generally the amount of culture is in the range of about $1 \times 10^{-1}$ to about $5 \times 10^2$ grams per liter of material being treated.

The following examples are provided to further illustrate the present invention.

EXAMPLE 1

Degradation of Batch-Fed Urea

About four liters of a standard dialysate solution of the following composition were prepared:

| Component | Concentration, g/l |
|---|---|
| Sodium chloride | 5.62 |
| Potassium chloride | 0.38 |
| Sodium acetate | 2.02 |
| Calcium chloride | 0.8 |
| Magnesium chloride | 0.2 |
| Dextrose | 1.0 |

To one liter of this solution, about 100 milligrams % of urea were added and the solution was used in a bioreactor containing 5 grams of a culture of the type identified as ATCC 31381. After one hour another gram of urea was added bringing the urea concentration back up to 100 mg %. The dialysate flow rate was 500 ml/min, the volume of the reactor was 1 liter, the temperature 35° C. and the aeration rate about 600 ml/min. The urea concentrations were determined by spectrographic analysis and the results are shown in FIG. 2. At the end of 100 minutes, all of the urea had been removed, providing degradation rates of $4 \times 10^{-3}$ mg urea-N/mg of culture-minute.

EXAMPLE 2

The use of 1.2 5 g/liter of the culture of type identified as ATCC 31381 to treat 3.8 liters of a dialysate of the composition described hereinabove and containing 200 mg % (200 mg/100 ml) of urea and operated under the conditions described in Example 1 resulted in 120 mg of urea being degraded per minute, a 0.024 mg. urea/mg culture-minute. About four liters of a standard dialysate solution were prepared of the composition set forth hereinabove in Example 1.

EXAMPLE 3

Urea, dissolved in dialysate, was infused at rates of 40 to 55 mg of urea nitrogen per minute directly into the bioreactor. The bioreactor assembly as well as the dialysate, described above, were employed for the continuous tests.

Dialysate flowrate was 500 ml/min, temperature 38° C., and the aeration rate was about 600 ml/min for all runs. Five, ten, or twenty grams of a culture of the type ATCC 31381 were added to the bioreactor at the start of each run. All culture additions in these and the above tests were from the same manufacture lot to remove any potential differences that might prevail in culture density and/or activity. The continuous tests ran from 160–180 minutes and the urea was measured as above. The results for 5, 10, and 20 grams of culture are shown in FIGS. 3, 4, and 5, respectively.

As would be expected, the greater the ATCC 31381 inoculum, the lower the urea levels in the bioreactor. For the lower inoculum levels, a lag phase, where no urea degradation is effected, might be present.

The rise and falls in the data might be due to a minimum concentration-time characteristics for the culture. It appears that about 20 mg % of urea-nitrogen may be required in the bath for a 90 minute induction period before maximum activity is reached. Prior to this period, the culture is viable and degrading urea, but not at a maximal rate. Once the induction phase is completed, the system is highly active.

Table 1 below describes the degradation of urea for the three levels of inocula. It is seen that the degradation rate (mg urea-N/min) increases with increased culture loading, but the specific rate (mg urea-N/mg culture-min) decreases. The fact that identical aeration rates were employed for all three types might explain this behavior. The higher loaded systems may not have had enough oxygen to maintain the high specific rates, but still effected higher degradation.

Table 1

| Urea Removal Rates for Continuous Systems | | | |
|---|---|---|---|
| ATCC 31381 type culture, loading in systems, grams | 5 | 10 | 20 |
| Degradation rate mg urea-N/min | 30 | 43.7 | 50.2 |
| Specific degradation rate mg urea-N/mg ATCC 31381-min | $6 \times 10^{-3}$ | $3.5 \times 10^{-3}$ | $2 \times 10^{-3}$ |

As apparent, the nitrogen metabolizing culture employed in the present invention are able to maintain the dialysate bath urea level at a manageable level. One of the most advantageous aspects of the culture is their ability to degrade nitrogenous compounds to gaseous products, leaving no residue within the culture. This makes the use of cultures of the type ATCC 31381 extremely compatible with the intended biomedical support scheme.

For other discussions of the present invention, see Ackerman et al, "The Use of Nitrifying Bacteria in a Recycling Dialysate Delivery System", presented at the 70th Annual Meeting of the AIChE, Nov. 13–17, 1977, New York, N.Y. Cultures employed in the present invention are commercially available under the trade designation AT5N.

What is claimed is:

1. A method for converting urea to inocuous products which comprises:
   a. obtaining a culture having the identification ATCC 31381, or at least one of its cultures selected from the group of Enterobacter agglomerans, Group D Streptococcus, Bacilli, and Pseudomonad or mixtures of said culture having the identification ATCC 31381 and said at least one of its cultures;
   b. adding said culture to a composition containing urea in an amount sufficient to degrade urea therein to inocuous product, and said culture and fluid being under aerobic conditions.

2. The method of claim 1 wherein said fluid contains at least 1 milligram/liter of dissolved oxygen.

3. The method of claim 1 wherein said fluid is a dialysate.

4. The method of claim 1 wherein said culture is added on a semisolid substrate of peanut hulls containing up to 12% by weight of a cereal grain based upon the weight of the peanut hulls.

5. The method of claim 1 wherein the temperature of the fluid during treatment is in the range of 0° to 40° C.

6. The method of claim 3 wherein the temperature of the fluid during treatment is in the range of 0° to 40° C.

7. The method of claim 1 wherein the amount of culture is in the range of about $1 \times 10^{-1}$ to about $5 \times 10^2$ grams per liter of said composition containing urea.

8. The method of claim 1 wherein said culture is a culture having the identification ATCC 31381.

* * * * *